US00PP32616P3

(12) United States Plant Patent
Randag

(10) Patent No.: US PP32,616 P3
(45) Date of Patent: Dec. 8, 2020

(54) CALLA LILY PLANT NAMED 'ALICE SPRINGS'

(50) Latin Name: *Zantedeschia sprengeri*
Varietal Denomination: Alice Springs

(71) Applicant: Dümmen Group B.V., De Lier (NL)

(72) Inventor: Cecilius Jan-Jochem Randag, CJ 'T Zand (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/602,415

(22) Filed: Sep. 30, 2019

(65) Prior Publication Data

US 2020/0113103 P1 Apr. 9, 2020

Related U.S. Application Data

(60) Provisional application No. 62/766,205, filed on Oct. 4, 2018.

(51) Int. Cl.
*A01H 5/02* (2018.01)
*A01H 6/10* (2018.01)

(52) U.S. Cl.
USPC ..... Plt./490
CPC ..... *A01H 6/10* (2018.05)

(58) Field of Classification Search
USPC ..... Plt./490
CPC ..... A01H 5/02
See application file for complete search history.

*Primary Examiner* — Kent L Bell
(74) *Attorney, Agent, or Firm* — The Webb Law Firm

(57) ABSTRACT

'Alice Springs' is a new variety of calla lily plant having light yellow colored spathes that produces 5-13 inflorescences per 14-16 cm tuber. The flower stems are about 44-53 cm in height. The leaves are green without whitish spots and have a leathery texture.

1 Drawing Sheet

Botanical classification: *Zantedeschia sprengeri*.
Varietal denomination: 'Alice Springs'.

BACKGROUND OF THE NEW PLANT

The present invention comprises a new and distinct cultivar of calla lily, botanically known as *Zantedeschia sprengeri* and hereinafter referred to by the cultivar name 'Alice Springs'.

'Alice Springs' is a product of a planned breeding program, which had the objective of creating *Zantedeschia* hybrids for pot flower production in a wide range of colors with a large, classic flower shape. The breeding program began in 1989, and the new cultivar is a seedling selected from the crossing of *Zantedeschia sprengeri* seedling Z020314 (female parent, unpatented) with *Zantedeschia sprengeri* seedling Z030217 (male parent, unpatented). 'Alice Springs' was selected in 2009 by the inventor in 't Zand, The Netherlands as one flowering plant within the progeny of the stated cross.

The first act of asexual reproduction of 'Alice Springs' by tissue culture was performed by the inventor in September of 2011 in 't Zand, The Netherlands. Subsequent asexual reproductions by tissue culture at the same location have demonstrated that the combination of characteristics as herein disclosed for the new cultivar are retained and reproduced true to type through successive generations of asexual reproduction.

The following observations, measurements and comparisons describe plants grown from 12 to 14 weeks in 14 cm pots in 't Zand, The Netherlands under greenhouse conditions, which approximate those generally used in horticultural practice. Color references are made to The 2001 R.H.S.

Colour Chart of The Royal Horticultural Society of London, 4$^{th}$ Edition, except where general color terms of ordinary significance are used.

The present invention has not been evaluated under all possible environmental conditions. The phenotype may vary with variations in environment without a change in the genotype of the plant.

The following traits have been repeatedly observed and determined to be basic characteristics of 'Alice Springs' which, in combination, distinguish this calla lily as a new and distinct cultivar:

1. Absence of leaf maculation;
2. Lanceolate leaf shape; and
3. Large inflorescences.

Table 1 provides a comparison of 'Alice Springs' to its parents, as well as *Zantedeschia sprengeri* variety 'Sunclub' (U.S. Plant Pat. No. 27,891).

TABLE 1

| Variety | Relationship | Trait differences | Description |
|---|---|---|---|
| 'Alice Springs' | New variety | Spathe color | Upper surface is between RHS 2A and 2B |
| | | Plant height | 44-53 cm |
| Z020314 | Female parent | Spathe color | Upper surface is between RHS 1A-1B |
| | | Plant height | 33-50 cm |
| Z030217 | Male parent | Spathe color | Between RHS 60D-61C |
| | | Plant height | 35-52 cm |
| 'Sunclub' | Known variety | Spathe color | Upper surface varies between RHS 12A-12B |
| | | Plant height | 15-45 cm |

BRIEF DESCRIPTION OF THE DRAWING

The accompanying photographic drawing illustrates the new variety, with the colors being as nearly true as is possible with color illustrations of this type.

DESCRIPTION OF THE NEW PLANT

Type: Deciduous.
Size:
- *Height of the leaf canopy above the soil.*—40-51 cm.
- *Height of top of inflorescences above the soil.*—44-53 cm.
- *Diameter.*—52-66 cm.

Form: Semi-spreading.
Number of inflorescences per tuber:
- *Size* 14-16 *cm in diameter.*—5-13 inflorescences.

Branches:
- *Number.*—Plentiful.
- *Color.*—Green Group RHS 141C.
- *Young shoot color.*—Green Group RHS 143C.

Leaves:
- *Size.*—Width: 8.5-10 cm, with the broadest part of the leaf blade far below the middle. Length: 22-24 cm.
- *Number per plant.*—19-29.
- *Leaf blade lobes.*—Present; having a length of 4.5-6.5 cm.
- *Shape.*—Lanceolate.
- *Apex.*—Apiculate.
- *Base.*—Rounded.
- *Margin.*—Entire; having a color of Green Group RHS 137B.
- *Color.*—Upper surface: Green Group RHS 137B, with no maculations present. Lower surface: Green Group RHS 137C, with no maculations present.
- *Veins.*—Configuration: Pinnate. Color: Green Group RHS 139C.
- *Surface texture.*—Smooth (both surfaces).
- *Petiole.*—Length: 20-25 cm. Diameter: Average of 24 mm. Color: The base is Greyed-Purple Group RHS 183B, the upper part is Yellow-Green Group RHS 144A.

Roots:
- *Color.*—White Group RHS 155D.
- *Branching description.*—Fibrous root system. Several main roots emerge from the top of the tuber and form a small number of lateral roots.

Spathe:
- *Size.*—Length (measured from opening to tip): 6.5-8.5 cm. Width: 5.5-8 cm. Height: 12-14 cm.
- *Color.*—Throat spot: Absent. Upper surface: Between Yellow Group RHS 2A and 2B. Lower surface: Yellow-Green Group RHS N144C.
- *Vein color.*—Yellow Group RHS 4A.
- *Shape.*—Funnel.
- *Apex.*—Acuminate.
- *Base.*—Attenuate.
- *Margin.*—Entire.

Spadix:
- *Shape.*—Cylinder.
- *Size.*—Length: 25-35 mm. Diameter: 15-20 mm.
- *Color.*—Yellow Group RHS 12A.
- *Position relative to spathe.*—Upright.
- *Female flower.*—Number: 20-40. Shape: Pyramid. Height: 2 mm. Diameter: 4 mm.
- *Male flower.*—Number: 200-250. Shape: Cone. Height: 1 mm. Diameter: 0.2 mm.

Peduncle:
- *Size.*—Length: 45-58 cm. Diameter: 20-25 mm.
- *Color.*—The upper and lower parts are Yellow-Green Group RHS 144A.
- *Texture.*—Smooth.

Reproductive organs:
- *Location of female organs.*—Basal position of the spadix.
- *Location of male organs.*—Upper position of the spadix.
- *Perianth.*—Conspicuous.
- *Stamens.*—Presence: Not visible before pollen release. Number: Between 480 and 600. Pollen amount: Abundant; similar to 'Picasso' (U.S. Plant Pat. No. 15,282). Color: Between White Group RHS 155B and 155C.
- *Anther.*—Shape: Round. Length: Less than 1 mm. Color: Between Yellow Group RHS 8B and 8C.
- *Filament.*—Length: Less than 1 mm. Color: Between White Group RHS 155C and 155D.
- *Pistils.*—Number: 15 to 30. Length beyond perianth: About 1 mm.
- *Stigma.*—Shape: Round. Size: Less than 1 mm.
- *Style.*—Length: Less than 1 mm. Color: Between Yellow Group RHS 8B and 8C.
- *Ovaries.*—Texture: Smooth. Length: Between 1 to 10 mm. Width: Between 1 to 10 mm. Color: The top color is Yellow Group RHS 9A, the bottom color is Yellow-Green Group RHS 150B.

Disease resistance: No unusual susceptibility/resistance to diseases noticed to date.
Pest resistance: No unusual susceptibility/resistance to pests noticed to date.
Heat tolerance: No heat tolerance.
Hardiness: Not hardy.
Flowering: In general, the time from planting to first flowering takes eight weeks.
Lastingness: About two weeks on the plant.
Fragrance: None.

I claim:

1. A new and distinct variety of calla lily plant named 'Alice Springs' as herein described and illustrated.

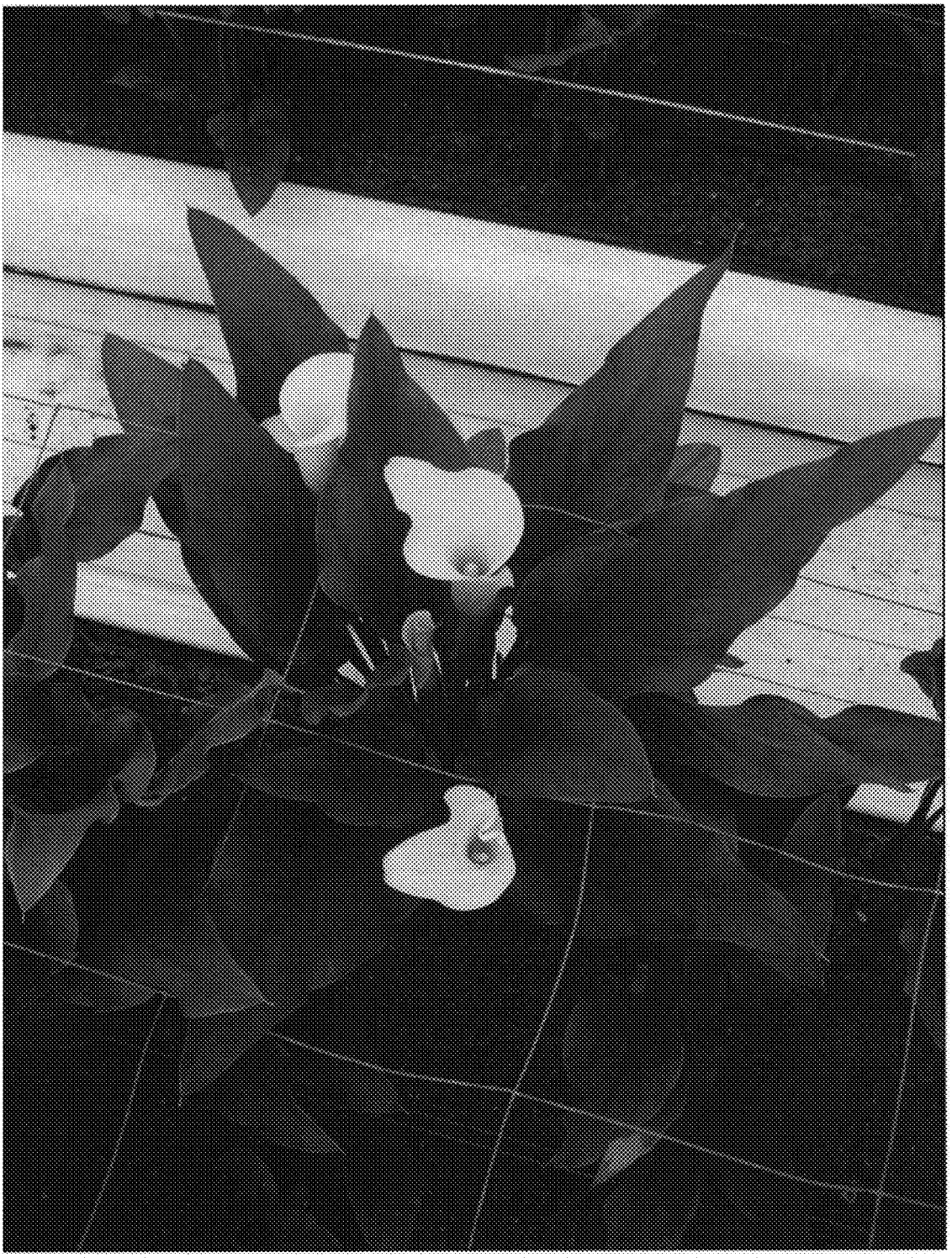

* * * * *